United States Patent [19]

Moss

[11] Patent Number: 4,704,111
[45] Date of Patent: Nov. 3, 1987

[54] NASOGASTRIC FEEDING TUBE

[76] Inventor: James P. Moss, 3617 Glenview Ave., Glenview, Ky. 40025

[21] Appl. No.: 898,751

[22] Filed: Nov. 20, 1985

Related U.S. Application Data

[63] Continuation of Ser. No. 487,764, Apr. 22, 1983.

[51] Int. Cl.[4] ............................................... A61M 5/00
[52] U.S. Cl. ..................................... 604/270; 604/280
[58] Field of Search ...................... 604/19, 27, 48, 82, 604/93, 102, 264, 270, 280–285, 9, 94, 266

[56]                References Cited

U.S. PATENT DOCUMENTS

| 2,887,109 | 5/1959 | Barrington | 604/262 |
| 3,399,668 | 9/1968 | Lundgren | 604/280 |
| 3,885,561 | 5/1975 | Cami | 604/280 |
| 3,888,249 | 6/1975 | Spencer | 604/247 |
| 4,410,320 | 10/1983 | Dykstra et al. | 604/270 |

FOREIGN PATENT DOCUMENTS

| 960932 | 1/1975 | Canada | 604/83 |
| 330284 | 12/1920 | Fed. Rep. of Germany | 604/264 |
| 1124980 | 11/1984 | U.S.S.R. | 604/48 |

Primary Examiner—Stephen C. Pellegrino
Attorney, Agent, or Firm—Larson and Taylor

[57] ABSTRACT

A nasogastric feeding tube for enteral alimentation or feeding within the intestine of a patient with a nutrient solution is disclosed. The feeding tube includes a dispensing tube which is located in the stomache of a patient. A number of slits are located along the dispensing tube and the nutrient solution is dispensed through these slits. A conducting tube is connected to the dispensing tube. The conducting tube passes out of the nose of the patient and is connected to a suitable source of nutrient solution. The conducting tube has a substantially smaller outside diameter than the outside diameter of the dispensing tube to provide greater patient comfort and fewer medical complications. A non-slitted portion of the dispensing tube is provided at the distal end thereof so that the distal end of the dispensing tube has sufficient inherent strength to be easily inserted into the nose of the patient. The distal end of the dispensing tube can also be provided with a weight. A radiopaque stripe and distance marks can further be provided on the conducting tube for accurate locating of the conducting tube and dispensing tube in the patient.

4 Claims, 1 Drawing Figure

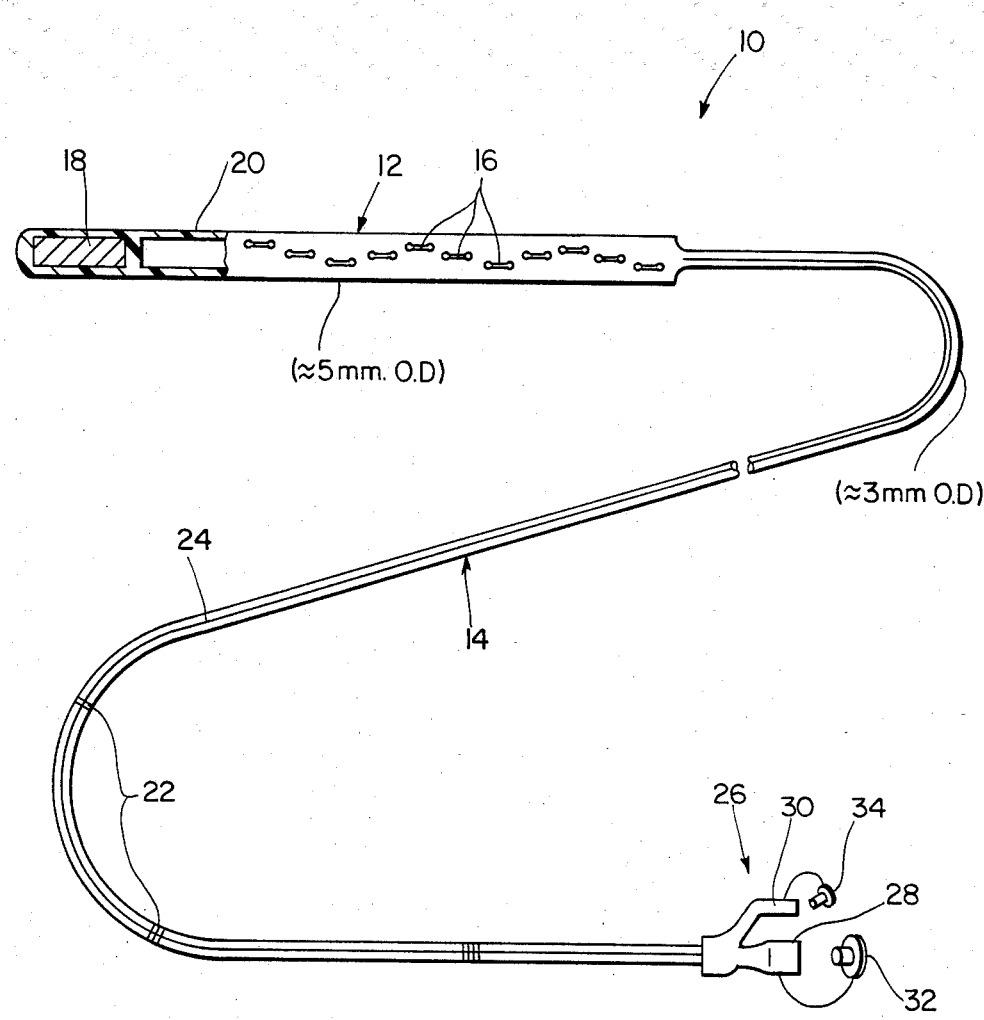

NASOGASTRIC FEEDING TUBE

This application is a continuation, of application Ser. No. 487,764 filed Apr. 22, 1983, now abandoned.

FIELD OF THE INVENTION

The present invention relates generally to enteral alimentation or intestinal feeding of a patient and more particularly to a nasogastric feeding tube used for enteral alimentation of a patient.

BACKGROUND OF THE INVENTION

The nutrition of medical and surgical patients has become a matter of clinical importance within the last decade. Since initial reports of parenteral nutrition of an infant in the mid-1960's nutritional support has been of inestimable value in reducing the mortality of serious diseases and the morbidity related to certain types of operations. Following the development of techniques for parenteral alimentation, especially intravenous feeding, interest has increased in enteral alimentation using the gastrointestinal tract. The use of specially defined chemical or elemental diets containing a known quantity of protein, amino acids, carbohydrates, and fat with low osmolality is as effective as intravenous nutritional support when the patient's gastrointestinal tract is intact and functioning. Although not suitable for all patients, enteral alimentation is safer, easier, and better accepted by the patient. In addition, enteral alimentation is more economical than parenteral alimentation. For example, the cost to administer 3,000 calories intravenously is over 10 times greater than the cost of supplying the same caloric support through enteral alimentation. Further, by using an intact gastrointestinal tract for alimentation, the major problems of sepsis and metabolic derangement which relate to intravenous alimentation are largely obviated. Another major advantage is that adequate nutritional support is greatly simplified.

Historically, polyvinyl chloride nasogastric tubes have been used to infuse special diets. These tubes have proven unacceptable for several reasons. One problem has been that gastric acid tends to migrate along the tube at the esophagogastric junction causing furrows and erosion of the mucosa in the distal esophagus. This can result in stenosis or hemorrhage. Larger tubes are also tolerated very poorly by the patient because of continuing nasopharyngeal irritation and patient discomfort. Recently, the use of small silicone rubber feeding tubes has proven advantageous in the administration of elemental diets. However, due to the uniformity of size and suppleness of the silicone rubber tubes, at times it has proven virtually impossible to pass these tubes through the nasopharynx into the esophagus and stomache. Various devices including sylets and the back of a wooden Q tip have been used to insert the tube, but are not satisfactory. At times, an empty capsule has been used to join the silicone rubber feeding tube to a larger nasogastric tube so that it can be passed through the nose and into the stomache. The tip of the tube has also been provided with holes through which the diet emerges and these holes act to reduce the strength of the tube and make insertion difficult. At the present time, the difficulty of introducing small silicone rubber and similar feeding tubes is the chief barrier to their use despite their medicinal advantages and improved patient care.

Various devices besides a simple tube have been proposed in the prior art to perform enteral alimentation. For example, in U.S. Pat. No. 1,736,182 (Wilkins), a stomache feeding tube having a mercury weighted end portion with holes adjacent to the weighted end is disclosed. Another prior art feeding tube is disclosed in U.S. Pat. No. 3,155,097 (Barron). This patent discloses a feeding tube having a looped lower end with holes therein for even dispersing of the liquid. The device disclosed in this patent also includes a gravity balloon weight which is partially filled with mercury. The use of a heat sealed polyvinyl chloride mercury filled capsule affixed to the distal end of a standard 42 inch polyvinyl chloride No. 8 F feeding tube with several additional side holes cut in the distal end is disclosed in an article by Boddie and Hoffmeister entitled "Continuous PumpTube Enteric Hyperalimentation" in Surgery, Genecology and Obstetrics, August 1976, Volume 143 at Page 273.

Other devices in the prior art have also been disclosed for delivering or removing a fluid from a patient's body. For example, in U.S. Pat. No. 4,068,664 (Sharp et al), a surgical suction wand assembly is disclosed having a tipped portion with holes therein which can be fitted to a smaller diameter tube. In U.S. Pat. No. 3,741,217 (Ciarico), a catheter is disclosed which has multiple inlet passages leading to a single main passageway. The use of slits or slots in place of holes at the end of the catheter have also been disclosed in U.S. Pat. Nos. 4,168,699 (Hauser), 4,129,129 (Amrine), and 3,885,561 (Cami). In order to indicate the position of a catheter, a radiopaque stripe on the catheter has been disclosed in U.S. Pat. No. 3,938,529 (Gibbons).

Although the prior art has disclosed feeding tubes and like devices, the prior art has not disclosed a feeding tube which is both comfortable to the patient, safe, and easy to insert.

SUMMARY OF THE INVENTION

In accordance with the present invention, a nasogastric feeding tube for enteral alimentation or intestinal feeding is disclosed. The feeding tube is both easy to insert, safe, and comfortable for the patient. The feeding tube includes a dispensing tube which is located in the stomach of the patient. The dispensing tube has a plurality of slits located along at least a portion of the length thereof and it is through these slits that the nutrient solution is dispensed. Connected to the dispensing tube at one end is a conducting tube. The conducting tube is connected at the other end to a source of the nutrient solution and the conducting tube passes from the stomach of the patient out of the nose of the patient. The conducting tube has an outside diameter which is substantially smaller than the outside diameter of the dispensing tube for greater patient comfort and safety.

In the preferred embodiment of the present invention, the dispensing tube also has a non-slitted portion located at the distal end thereof. By providing this non-slitted portion, the distal end of the dispensing tube has sufficient inherent strength to be easily inserted in the nose of the patient. In addition, a weight is located at the distal end of the dispensing tube to facilitate placement in the stomach of the patient. In order to easily locate the dispensing tube in the stomach of the patient, distance marks are spaced along the length of the conducting tube. Also, a radiopaque stripe is located along the length of the conducting tube so that the exact location can be determined if needed. Preferably, both the dispensing tube and conducting tube are made of silicone rubber and the other end of the conducting tube is equipped with a double ended connector so that both the source of nutrient fluid and a source of other medicinal fluid are connectable to the conducting tube.

Other features and advantages of the present invention are stated in or apparent from the detailed description of a presently preferred embodiment of the invention found hereinbelow.

BRIEF DESCRIPTION OF THE DRAWINGS

The single FIGURE is a perspective view of the feeding tube of the present invention.

DETAILED DESCRIPTON OF THE PREFERRED EMBODIMENT

With reference now to the single FIGURE, a feeding tube 10 is depicted and includes a dispensing tube 12 and a conducting tube 14. As shown, conducting tube 14 is substantially smaller than dispensing tube 12. It is contemplated that conducting tube 14 would have an outside diameter of approximately 3 mm, while dispensing tube 12 would have outside diameter of 4 to 5 mm. It is also contemplated that dispensing tube 12 would have an overall length of approximately 18 cm and that conducting tube 14 would have an overall length of approximately 120 cm. This length of conducting tube 14 allows the end of conducting tube 14 to be connected to the source of nutrient solution at a location away from the head of the patient to improve patient comfort while resting and sleeping.

Dispensing tube 12 is provided with a plurality of slits 16 as shown. Located at the end of dispensing tube 12 remote from conducting tube 14 is a weight 18. Weight 18 can be a sealed mercury weight or tungsten for example. It should be noted that dispensing tube 12 includes a non-slitted portion 20 located adjacent weight 18. It is contemplated that non-slitted portion 20 would be approximately 1.5 cm in length.

Conducting tube 14 has a series of distance marks 22 located along the length thereof. Distance marks 22 are used to indicate the length of feeding tube 10 from weight 18 to the particular distance mark of interest. By use of distance marks 22, feeding tube 10 can be inserted the appropriate length to approximately locate a dispensing tube 12 in the stomach of the patient. In order to confirm the location of dispensing tube 12 in the stomach of the patient or to more accurately locate dispensing tube 12, conducting tube 14 is also provided with a radiopaque stripe 24 along the entire length thereof. Provided at the end of conducting tube 14 remote from dispensing tube 12 is a double-ended fluid connector 26. Double-ended connector 26 is provided with a large hose adapter 28 and a small hose adapter 30. Both hose adapters 28 and 30 are provided with suitable plugs 32 and 34, respectively.

Feeding tube 10 is used in the following manner. Initially, dispensing tube 12 is grasped and the end containing weight 18 is inserted in one nostril of the patient. Be providing dispensing tube 12 with non-slitted portion 20, and by having dispensing tube 12 of sufficient outside diameter, the end of dispensing tube 12 containing non-slitted portion 20 has sufficient inherent strength to be introduced through the nasal cavity into the esophogus and swallowed with ease. Weight 18 exerts a slight downward force on dispensing tube 12 and helps the patient to swallow both dispensing tube 12 and conducting tube 14. Dispensing tube 12 and conducting tube 14 are allowed to be swallowed by the patient until dispensing tube 12 is approximately located in the stomach of the patient. The location of dispensing tube 12 can be estimated from the distance marks 22 located on conducting tube 14 which indicates the length of feeding tube 10 which has been inserted into the patient. If exact positioning of dispensing tube 12 is needed, or if there is some doubt as to the position of dispensing tube 12, a x-ray of the patient can be taken. The x-ray picture then clearly shows radiopaque stripe 24 on conducting tube 14 so that the exact location of dispensing tube 12 is easily determined. From this determination, the location of dispensing tube 12 can be adjusted. Once dispensing tube 12 is properly located, plug 32 is removed from large hose adapter 28 and a suitable source of nutrient fluid is connected to large hose adapter 28. The nutrient fluid then passes through conducting tube 14 and into dispensing tube 12. From dispensing tube 12, the nutrient fluid flows out through slits 16 and into the stomach of the patient. It should be noted that slits 16 are located over a portion of the length of dispensing tube 12 so that the nutrient solution is evenly dispersed in the stomach. In addition, slits 16 are less likely to clog than circular holes and are preferred for that reason. In this preferred embodiment, each slit 16 is formed from two circular holes which are connected by a narrow opening. The provision of a plurality of slits 16 helps prevent malfunction from occlusion which occurs more commonly where a limited number of openings are present. As large hose adapter 28 is being used, it is also possible to administer an elemental diet, antibiotic suspensions, or other medical suspensions through small hose adapter 30 without disconnecting the nutrient supply. The access provided by small hose adapter 30 can also be used for periodic irrigation of the feeding tube to eliminate stasis and reduce the incidence of plugging.

With dispensing tube 12 in place, the smaller silicone rubber body of conducting tube 14 passes from the stomach through the esophagogastric junction. The small size and lack of tissue reactivity of conductihg tube 14 reduces esophageal erosion. The small size of conducting tube 14 as it emerges through the posterior pharynx and out through the nose makes it better tolerated by the patient over a longer period. The length of conducting tube 14 is also sufficient so that the connection of conducting tube 14 to the source of nutrient solution is away from the patient's head. This improves patient comfort while resting and sleeping.

While the invention has been described in detail with respect to an exemplary embodiment thereof, it will be understood by those of ordinary skill in the art that variations and modifications may be effected in the exemplary embodiment within the scope and spirit of the invention.

I claim:

1. A nasogastric feeding tube for enteral alimentation of a patient with a nutrient solution comprising:
    an integral tube including a dispensing tube portion and conducting tube portion, the dispensing tube portion having an outside diameter larger than the outside diameter of the conducting tube portion,
    means forming a plurality of slits in said dispensing tube portion located along at least a portion of the length thereof so as to define a slitted portion of said dispensing tube through which the nutrient solution is dispensed, said slit forming means comprising for each slit a pair of spaced circular holes with said spaced holes being interconnected with a longitudinally extending narrow opening to prevent malfunction of the tube from occlusion of the openings, the distal end of the dispensing tube portion being unslitted to provide sufficient inherent strength to be easily inserted into the nose of the patient, a weight disposed in the distal end of the dispensing tube portion, the conducting tube portion having the proximal end adapted to be connected to a source of nutrient solution, the conducting tube portion adapted to pass out of the nose of a patient.

2. A nasogastric feeding tube as claimed in claim 1 further including a radiopaque stripe located along the length of said conducting tube portion.

3. A nasogastric feeding tube as claimed in claim 1 further including distance marks located at spaced intervals along the length of said conducting tube portion.

4. A nasogastric feeding tube as claimed in claim 1 further including a double-ended fluid connector located at the other end of said conducting tube portion, one of the ends of said double-ended connector being normally attached to the source of nutrient fluid and the other end of said double-ended connector normally having a removable plug inserted therein whereby after removal of the plug other sources of medicinal fluids are connectable to said conducting tube portion.

* * * * *